United States Patent
Parsons et al.

(10) Patent No.: US 10,578,556 B2
(45) Date of Patent: Mar. 3, 2020

(54) ASSAY DEVICE EMPLOYING FLUORESCENT LABELS

(71) Applicant: Ellume Pty Ltd, East Brisbane, Queensland (AU)

(72) Inventors: Sean Andrew Parsons, East Brisbane (AU); Michael Stuart Hazell, Cambridge (GB); David Lara, London (GB)

(73) Assignee: Ellume Limited, East Brisbane (AU)

( * ) Notice: Subject to any disclaimer, the term of this patent is extended or adjusted under 35 U.S.C. 154(b) by 208 days.

(21) Appl. No.: 14/899,085

(22) PCT Filed: Jun. 18, 2014

(86) PCT No.: PCT/AU2014/050079
§ 371 (c)(1),
(2) Date: Dec. 16, 2015

(87) PCT Pub. No.: WO2014/201520
PCT Pub. Date: Dec. 24, 2014

(65) Prior Publication Data
US 2016/0370293 A1    Dec. 22, 2016

(30) Foreign Application Priority Data
Jun. 19, 2013  (AU) ............................. 2013902222

(51) Int. Cl.
*G01N 21/64* (2006.01)
*G01N 33/487* (2006.01)
(Continued)

(52) U.S. Cl.
CPC ....... *G01N 21/6428* (2013.01); *G01N 21/255* (2013.01); *G01N 21/645* (2013.01);
(Continued)

(58) Field of Classification Search
None
See application file for complete search history.

(56) References Cited

U.S. PATENT DOCUMENTS 7,489,403 B1    2/2009  Lin et al.
2005/0036148 A1*  2/2005  Phelan ............... G01N 21/4738
                                                356/446
(Continued)

FOREIGN PATENT DOCUMENTS

CN    101393197 A    3/2009
CN    101592659 B    8/2012
(Continued)

OTHER PUBLICATIONS

International Search Report and Written Opinion for Application No. PCT/AU2014/050079, dated Sep. 11, 2014, 14 pages.
(Continued)

*Primary Examiner* — Neil N Turk
(74) *Attorney, Agent, or Firm* — Morgan, Lewis & Bockius LLP

(57) ABSTRACT

An assay device is disclosed comprising a housing (10) and a test portion (2), electronic circuitry (30) and an optical assembly (41), each at least partially located in the housing (10). The test portion (2) comprises one or more test zones (2E, 2F) adapted to receive an analyte (22) and a fluorescent label associated with the analyte, the fluorescent label being excitable by excitation light and adapted to emit emission light upon excitation by excitation light. The electronic circuitry (30) comprises one or more light sources (31, 32) and one or more light detectors (33). The optical assembly (41-44) comprises one or more excitation light guides (41, 44) adapted to guide excitation light from the one or more light sources (31, 32) to the one or more test zones (2e, 2f), and/or one or more emission light guides (43, 44) adapted to guide emission light from the one or more test zones (2e, 2f)

(Continued)

to the one or more light detectors (33). The sets of emission light guides (43, 44) and excitation light guides (41, 44) may also take the form of individual integral one-piece light guide units where the emission light guide unit rests within the excitation light guide unit.

30 Claims, 8 Drawing Sheets

(51) Int. Cl.
  *G01N 21/25* (2006.01)
  *G01N 21/84* (2006.01)
  *G02B 7/02* (2006.01)
(52) U.S. Cl.
  CPC ..... *G01N 21/8483* (2013.01); *G01N 33/4875* (2013.01); *G02B 7/02* (2013.01); *G01N 2021/6439* (2013.01); *G01N 2021/6463* (2013.01); *G01N 2021/6465* (2013.01); *G01N 2021/6478* (2013.01); *G01N 2021/6484* (2013.01)

(56) References Cited

U.S. PATENT DOCUMENTS

| | | | |
|---|---|---|---|
| 2005/0036728 A1* | 2/2005 | Braunisch | G02B 6/00 385/14 |
| 2005/0083522 A1 | 4/2005 | Aravanis et al. | |
| 2005/0095697 A1 | 5/2005 | Bachur, Jr. et al. | |
| 2006/0148103 A1* | 7/2006 | Chen | B82Y 5/00 436/524 |
| 2006/0275920 A1 | 12/2006 | Petrilla et al. | |
| 2007/0116595 A1 | 5/2007 | Petrilla et al. | |
| 2009/0027682 A1 | 1/2009 | Hebert et al. | |
| 2009/0211345 A1 | 8/2009 | Nahm et al. | |
| 2010/0009395 A1 | 1/2010 | Ramanujam et al. | |
| 2010/0061894 A1 | 3/2010 | Yamauchi | |
| 2010/0135857 A1 | 6/2010 | Hunter et al. | |
| 2012/0035705 A1 | 2/2012 | Giasolli et al. | |

FOREIGN PATENT DOCUMENTS

| | | | |
|---|---|---|---|
| EP | 2031376 A2 | 3/2009 | |
| JP | H 2-903 | 1/1990 | |
| JP | H 3-503453 A | 8/1991 | |
| JP | 2004-521714 A | 7/2004 | |
| JP | 2006-119065 A | 5/2006 | |
| JP | 2006-526778 A | 11/2006 | |
| JP | 2007-509324 A | 4/2007 | |
| JP | 2007-316486 A | 12/2007 | |
| JP | 2008-514383 A | 5/2008 | |
| JP | 2008-170190 A | 7/2008 | |
| JP | 2008-261842 A | 10/2008 | |
| JP | 2010-539484 A | 12/2010 | |
| JP | 2013-002851 A | 1/2013 | |
| JP | 2013-507615 A | 3/2013 | |
| WO | WO-2000/071991 A1 | 11/2000 | |
| WO | WO-2002/039096 A1 | 5/2002 | |
| WO | WO-2012/168703 A1 | 12/2012 | |
| WO | WO-2013092766 A1 * | 6/2013 | ......... G01N 21/6428 |

OTHER PUBLICATIONS

Japanese Office Action from Japanese Patent Application No. 2016-520198, dated May 15, 2018, 4 pages.
Japanese Office Action from Japanese Patent Application No. 2016-520198, dated Dec. 19, 2017, 6 pages.
Extended European Search Report from European Patent Application No. 14813557.7, dated Feb. 3, 2017, 9 pages.
English language translation of Chinese Office Action from Chinese Patent Application No. 201480035456.X, dated Jan. 31, 2018, 11 pages.

* cited by examiner

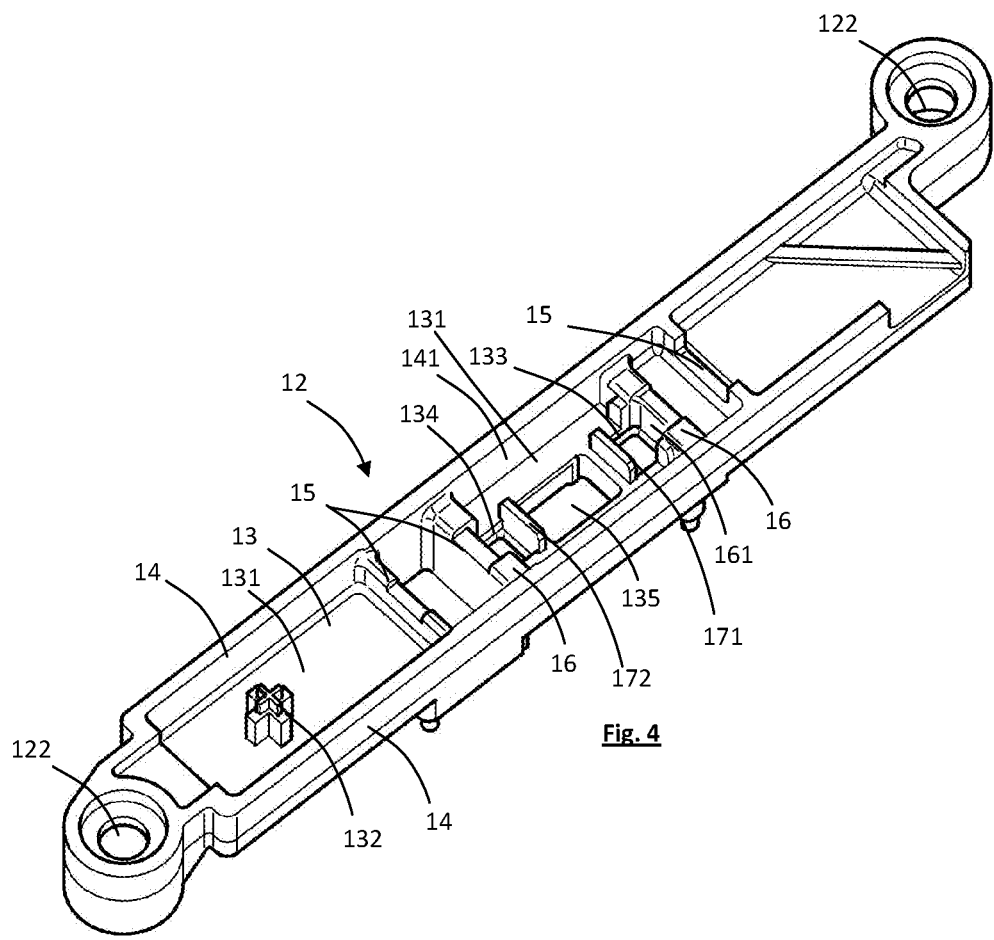
Fig. 4
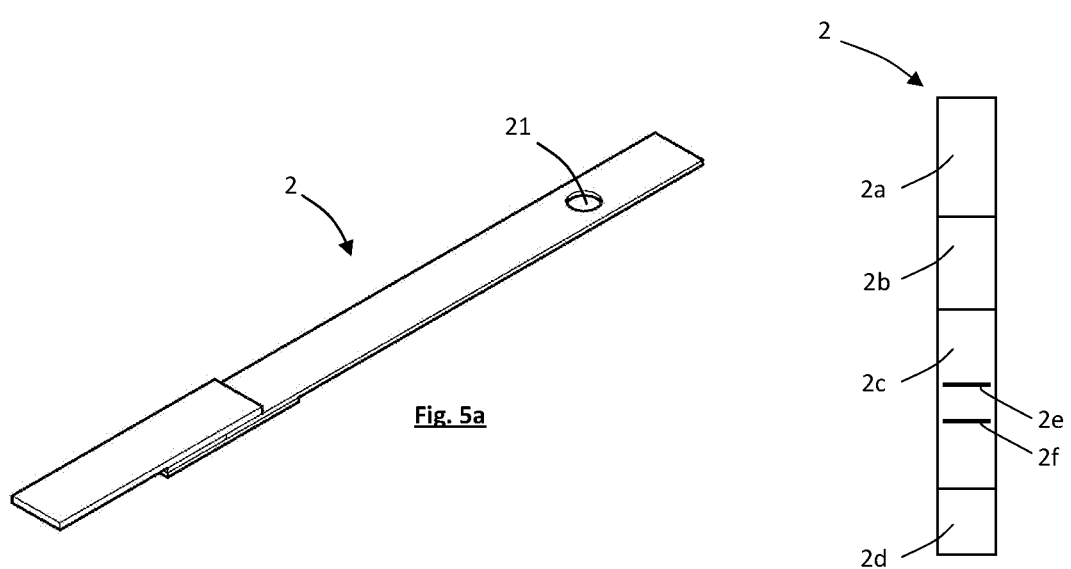
Fig. 5a
Fig. 5b

ASSAY DEVICE EMPLOYING FLUORESCENT LABELS

CROSS-REFERENCE TO RELATED APPLICATIONS

The present application claims priority from Australian provisional patent application no. 2013902222 filed on 19 Jun. 2013, the contents of which are incorporated herein by reference in their entirety.

TECHNICAL FIELD

The field of the present disclosure relates to devices and methods for determination of the presence, absence or amount of a biological entity in a human or animal body.

BACKGROUND

There exist many types of diagnostic devices for identifying target analytes and therefore target medical conditions in a person or animal. Increasingly, these devices are being designed for home use. The devices analyse a biological sample provided by the person or animal, such as a urine sample, blood sample or otherwise, and identify an analyte in the sample that provides a marker for the target condition.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to a first aspect, the present disclosure provides an assay device comprising:

a housing; and a test portion, electronic circuitry and an optical assembly, each a least partially located in the housing; wherein the test portion comprises one or more test zones adapted to receive an analyte and a fluorescent label associated with the analyte, the fluorescent label being excitable by excitation light and adapted to emit emission light upon excitation by excitation light;

the electronic circuitry comprises one or more light sources and one or more light detectors; and the optical assembly comprises one or more excitation light guides adapted to guide excitation light from the one or more light sources to the one or more test zones, and/or one or more emission light guides adapted to guide emission light from the one or more test zone to the one or more light detectors.

In one embodiment, the optical assembly includes one or more excitation light guides and one or more emission light guides.

The excitation and emission light guides may perform multiple functions. In addition to guiding light to and from the test zones, the light guides may also have a spectral filtering function and may focus, collimate and/or diverge light.

The one or more of the excitation light guides may be adapted to guide (transmit) excitation light that has a wavelength in an excitation wavelength band, and substantially block light that has a wavelength outside the excitation wavelength band. Additionally or alternatively, the one or more emission light guides may be adapted to guide (transmit) emission light that has a wavelength in an emission wavelength band and substantially block light that has a wavelength outside the emission wavelength band.

To achieve this spectral filtering, one or more of the excitation and emission light guides may comprise a light transmitting material impregnated with a filtering material such as a spectral filtering dye. A single dye or a mixture of dyes (a compound dye) may be employed in one or more of the light guides to achieve desired spectral filtering properties. Nevertheless, alternative approaches to spectral filtering may be employed, e.g., through use of additional filter elements, filter coatings and/or dichroic mirrors on the light guides or otherwise.

In general, the excitation wavelength band may have a relatively low wavelength and the emission wavelength band may have a relatively high wavelength. Accordingly, in one embodiment the excitation light guides may provide a short pass filter and the emission light guides may provide a long pass filter. At a general level, providing relatively large differences between central wavelengths of the transmission bands of the different light guides can ensures that higher discrimination between the excitation light and the emission light is possible during spectral filtering. Most notably, it can allow a significant reduction in the amount of excitation light that could be incident on the light detector. It may ensure that, to the greatest extent possible, the only light that is incident on the light detector is light emitted from fluorescent labels at the test zone.

By employing fluorescent labels, sensitivity gains may be achieved over more commonly deployed labels in assays, such as gold nanoparticles (colloidal gold). Further, sensitivity gains can be achieved by employing a fluorescent label that exhibits a relatively large Stokes shift. For example, the excitation wavelength band and the emission wavelength band may have central or peak wavelengths that are at least 200 nm apart, or at least 250 nm apart, or at least 300 nm apart, or at least 350 nm part or otherwise. For example, the excitation wavelength band may have a peak wavelength between 325 and 500 nm and the emission wavelength band may have a peak wavelength between 650 and 850 nm. In one embodiment, the excitation wavelength band has a peak wavelength of about 420 nm and the emission wavelength band has a peak wavelength of about 800 nm. An example of a flurophore that can exhibit a relatively large Stokes shift (e.g., a shift of greater than 250 nm, or greater than 300nm, or greater than 350 nm) is a quantum dot. In general, therefore, quantum dots can be used as fluorescent labels in devices of the present disclosure. However, other types of fluorescent labels may be used.

It has been found that quantum dots with higher peak excitation wavelengths generally exhibit larger Stokes shifts. Quantum dots that exhibit relatively large Stokes shifts may have peak excitation wavelengths of e.g., greater than 600 nm, greater than 650 nm, greater than 700 nm, or greater than 750 nm, or about 800 nm, for example. By employing fluorescent labels with relatively large Stoke shifts, and/or with relatively high peak emission wavelengths, problems associated with autofluorescence may be minimised. Autofluorescence may occur within a variety of substances within an assay device, such as the substrate of a test strip and backing layers, etc. Typically autofluorescence occurs with excitation and emission wavelength levels below about 650 nm. Therefore, by employing fluorescent labels that exhibit relatively large Stokes shifts and/or fluoresce above e.g., 650 nm, separation/filtering of any autofluorescent emission light from the fluorescent label emission light (i.e. from the emission light of interest) can be more straightforward to achieve. Furthermore, when the peak wavelength is e.g., above about 650 nm, the filtering may need only block wavelengths below the peak wavelength of the fluorescent label, since autofluorescence may substantially occur only at wavelengths below the peak wavelength of the fluorescent label. In contrast, if a fluorescent label such as Europium is employed, for example, which has a peak emission wavelength of about 615 nm, filtering of autofluorescence light can pose more considerable problems.

An alternative method of minimising the effects of autofluorescence that may be employed is Time Resolved Fluorescence. However, while this is effective at reducing the autofluorescence background, it has several major disadvantages relating to, for example, the complexity of the electronics needed to carry out the technique and the ability to integrate signals over time to any great degree.

According to a second, the present disclosure provides an assay device comprising:
a housing; and
a test portion, electronic circuitry and an optical assembly, each a least partially located in the housing; wherein
the test portion comprises
a plurality of fluorescent quantum dots adapted to associate with at least one analyte, the quantum dots being configured to emit fluorescent emission light at a peak wavelength of 650 nm or greater, and
one or more test zones,
wherein
the one or more test zones are adapted to receive the analyte and the fluorescent quantum dots associated with the analyte;
the electronic circuitry comprises one or more light sources to provide excitation light to the one or more test zones, and one or more light detectors to detect fluorescent emission light from the quantum dots at the one or more test zones; and
the optical assembly comprises one or more excitation light guides adapted to guide excitation light from the one or more light sources to the one or more test zones, and/or one or more emission light guides adapted to guide emission light from the one or more test zones to the one or more light detectors.

The assay device of the second aspect may have any one or more features of the assay device described with respect to the first aspect. As indicated above, it has been determined that quantum dots with higher peak emission wavelengths exhibit larger Stokes shifts and problems associated with autofluorescence can therefore be reduced. Accordingly, by employing a quantum dot that is adapted to emit emission light at a peak wavelength of 650 nm or greater, sensitivity of the assay device can be improved. As indicated above, the quantum dot may have a peak emission wavelength that is greater than 650 nm, greater than 700 nm, greater than 750 nm, or about 800 nm, or otherwise.

In any of the aspects disclosed herein, to further reduce the amount of excitation light, or other non-emission light, incident on the light detector, the assay device may comprise one or more light baffles. The light baffles may act to shield light from different parts of the assay device. The assay device may comprise a housing and the light baffles may form part of the housing. The light baffles may be located between the light sources and the light detectors, and/or between the excitation and emission light guides.

The optical path lengths through the light guides may be chosen to ensure that that they are sufficiently long for an adequate amount of spectral filtering to take place, depending on the spectral absorptivity and concentration of any spectral filtering dye impregnated therein, for example, and to ensure that they are sufficiently short to avoid undue loss of light due to higher than intended absorption. A variety of different optical path lengths may be present in the same light guide, depending on the possible entry and exit points of light from the light guide. However, the light guides may be configured so that there is a reasonably narrow distribution of possible path lengths.

The one or more excitation light guides may comprise a light collimator lens adjacent at least one of the light sources, in order to collimate light arriving from the light source into the excitation light guide. The one or more excitation light guides may also comprise refractive and/or reflective surfaces. The one or more excitation light guides may comprise a light exit face. The one or more test zones may be located on a substrate, e.g., a lateral flow test strip, and the light exit face may extend across a plane that is substantially perpendicular to a plane of the substrate on which the test zones are located. At least one refractive and/or reflective surface may be provided at a substantially opposite side of the light guide to the light exit face. The at least one refractive and/or reflective surface may be curved. A best fit plane extending through the curved surface may be at an angle from the plane of the light exit face. The angle may be between about 20 and 70 degrees, or between 30 and 45 degrees or otherwise. The curved surface may extend substantially an entire length of the light guide in a direction between electronic circuitry and the test portion. In general, the excitation light guides, including the refractive and/or reflective surfaces, may route excitation light efficiently between the light sources and the test zones. The refractive and/or reflective surfaces may act as a combined folding mirror and lens, providing optical power to the excitation light.

The one or more emission light guides may include curved refractive surfaces at one or both ends of the light guides. For example, at one or both ends of the light guides, a lens may be provided, e.g., a ball lens, a half ball lens or a plano-convex lens. A spacer may be provided between the lenses. The spacer may be a cylindrical spacer. The spacer may provide a total-internal-reflection concentrator between the two lenses.

The one or more test zones may comprise at least first and second test zones. The optical assembly may comprise at least first and second excitation light guides and first and second emission light guides. The first excitation light guide may be adapted to guide light from the at least one light source to the first test zone and the first emission light guide may adapted to guide light from the first test zone to the at least one light detector. The second excitation light guide may be adapted to guide light from the at least one light source to the second test zone and the second emission light guide may be adapted to guide light from the second test zone to the at least one light detector.

By providing at least two test zones, the device may be used to test for the presence of different analytes in a biological sample. For example, the first test zone may be adapted to receive a first analyte and the second test zone may be adapted to receive a second analyte. In one embodiment, the first analyte may be influenza A (e.g., a nucleoprotein of influenza A) and the second analyte may be influenza B (e.g., a nucleoprotein of influenza B). Nevertheless, a variety of different analytes may be tested using the device according to the present disclosure.

While providing at least two test zones may allow for testing of the presence of different analytes, as an alternative approach, one of the test zones may be provided as a control. Where target analytes such as influenza A and influenza B are to be detected, since the presence of one of these analytes in a body is generally understood to be mutually exclusive of the presence of the other of these analytes in the body, one of the two test zones can be used to perform a control function. For example, background fluorescence or autofluorescence can be deduced from the test zone that does not have a fluorescently labelled target analyte bound thereto, and the value of this fluorescence can be considered when determining a degree of fluorescence attributable to the presence of fluorescently labelled target analyte at the other of the test zones.

A single light source may provide excitation light for both the first and second test zones. Alternatively, a plurality of light sources may be provided. For example, the one or more light sources may comprise at least first and second light sources, wherein the excitation light guided by the first excitation light guide is from the first light source and the excitation light guided by the second excitation light guide is from the second light source.

The first and second emission light guides may guide emission light from the first and second test zones to the same light detector. Thus, a light detector may be shared between both the portion of the optical assembly associated with the first test zone and the portion of the optical assembly associated with the second test zone. By using a single light detector, the size of the device and the manufacturing costs can be reduced. So that a single light detector can be used that can differentiate between light emitted from the first and second test zones, the first and second light sources may be 'polled' in turn. In other words, the first and second light sources may be turned substantially on or off at different times such that a time division multiplexed signal is effectively received by the light detector. As one example alternative approach, the device may be configured such that light of different frequencies is emitted from the test zones (e.g., by employing labels with different fluorescent properties adapted to be received at the different test zones). The light detector may be a frequency dependent photodetector that can differentiate between the signal strengths of light of different frequencies. To this end, a wavelength division multiplexed signal may effectively be received by the light detector.

Nonetheless, the assay device may comprise more than one photodetector. For example, first and second photodetectors may be provided that are adapted to receive emission light from the first and second test zones respectively.

Particularly, although not necessarily exclusively, when a single light detector is provided that is adapted to receive emission light from both the first and second test zones, the light detector may be located between the first and second light sources. Thus, the first and second light sources may be located on opposite sides of the at least one light detector. The optical assembly can direct light centrally from the light sources toward the at least one light detector.

The assay device may be a hand-held device. The device may differ in this regard from apparatus employed in a laboratory environment. The assay device may be a rapid diagnosis point-of-care test device, permitting testing in less than one hour, less than 30 minutes, less than 10 minutes, less than 5 minutes, or less than 2 minutes, for example. The device may be disposable, configured for single-use only. The device may be provided in sterile packaging prior to use. The device may provide a means for entirely non-invasive testing. The device may be used for testing in the veterinary field as well as in the field of human medicine.

The electronic circuitry and optical assembly can form part of an electronic reader, adapted to determine the results of testing at the test portion. The reader may include a computer processor.

The test portion may be a lateral flow test strip or another device, element or assembly that provides a change in fluorescence at an illuminated test zone when a target analyte is determined to be present in a biological sample.

The device may comprise a display and the electronic circuitry, e.g., a processor of the electronic circuitry, may be connected to the display such that results of testing can be presented on the display.

In the present disclosure, the test portion may be fixed relative to the electronic circuit and the optical assembly. In this regard, the assay device may be provide for a 'fixed optics' solution to analyse the test portion. The position of the electronic circuitry, optical circuitry and test portions may be fixed during the manufacturing process and prior to receipt of a biological sample on the assay device. The device may differ in this regard from apparatus in which the test portion is moved relative to an electronic reader, and/or from apparatus in which a test portion is inserted into a reader after receipt of a sample for testing. In one embodiment, the test portion of the present disclosure may comprise a registration hole adapted to receive a protuberance that may extend, for example, from the housing. By locating the protuberance in the registration hole, the test portion may be positioned in appropriate fixed relationship relative to the other components of the device. Furthermore, by providing a registration hole, during manufacture of the test portion, the hole may be used to align the strip with equipment that forms the test zones on the test portion.

The device may comprise chambers separated by the light baffles, e.g., a first chamber and a second chamber separated by a first light baffle, and a third chamber separated from the second chamber by a second light baffle. The first light source may be configured to emit light into the first chamber and the second light source may be configured to emit light into the third chamber. The first excitation light guide may be located in the first chamber and the second excitation light guide may be located in the third chamber. The at least one light detector may be configured to receive light from the second chamber. Both the first and second emission light guides may be located in the second chamber. Whether separated by light baffles or otherwise, the excitation light guides and the emission light guides may be connected to each other, e.g., by elongate elements such as arms or tie bars. By connecting various components of the optical assembly to each other, rather than only to the housing or other part of the device, for example, registration of components within the optical assembly can be easier to achieve and/or can be more accurate. Furthermore, elements of the optical assembly may be larger, making handling, manufacture and assembly more straightforward.

The device may comprise an excitation light guide unit that comprises the first and second excitation light guides. The first and second excitation light guides may be one-piece, integrally formed in the excitation light guide unit. The excitation light guide unit may be moulded in one-piece, for example. The excitation light guide unit may be formed entirely of homogenous material.

Similarly, the device may comprise an emission light guide unit comprising the first and second emission light guides. The first and second emission light guides may be one-piece, integrally formed in the emission light guide unit.

The emission light guide unit may be moulded in one-piece, for example. The emission light guide unit may be formed entirely of homogenous material.

The first and second excitation light guides may be formed of a first material and the first and second emission light guides may be formed of second material different from the first material.

The excitation light guide unit may be connected to the emission light guide unit. At least one of the excitation light guide unit and the emission light guide unit may have a receiving portion adapted to receive the other of the excitation light guide unit and the emission light guide unit, for example. This may permit reliable registration of the two units during the manufacturing process. Again, it may also allow for reductions in the size of the device. In one embodiment, the first and second excitation light guides are provided at substantially opposite ends of the excitation light guide unit and the excitation light guide unit comprises one or more elongate elements that connect the first and second excitation light guides together. In combination, the one or more elongate elements and the first and second excitation light guides may define a recess therebetween. The emission light guide unit can be located in the recess. In one embodiment, the excitation light guide unit comprises two of the elongate elements that are adapted to locate on opposite sides of the emission light guide.

According to a third aspect of the present disclosure, there is provided an emission light guide unit for an assay device having a test portion and a light detector, the emission light guide unit comprising:
 a first emission light guide; and
 a second emission light guide;
 wherein the first and second emission light guides are formed in one-piece, and wherein the first emission light guide is adapted to guide fluorescent emission light from a first test zone of the test portion to the light detector, and the second emission light guide is adapted to guide fluorescent emission light from a second test zone of the test portion to the light detector.

According to a fourth aspect of the present disclosure, there is provided an emission light guide unit for an assay device having a test portion and a light detector, the emission light guide unit comprising:
 a first emission light guide; and
 a second emission light guide;
 wherein the first and second emission light guides are fixed together, and wherein the first emission light guide is adapted to guide fluorescent emission light from a first test zone of the test portion to the light detector, and the second emission light guide is adapted to guide fluorescent emission light from a second test zone of the test portion to the light detector.

The emission light guide unit and/or the first and second emission light guides of the third and fourth aspects may be configured in accordance with the emission light guide unit and/or the first and second emission light guides described above with respect to the first and second aspects. For example, the first and second emission light guides may each include curved refractive surfaces at one or both ends of the light guides. At one or both ends of each light guide, a lens may be provided, e.g., a ball lens, half ball lens or a plano-convex lens. A spacer may be provided between the lenses. Convex surfaces of the lenses may project from ends surfaces of the spacer. The spacer may be a cylindrical spacer. The spacer may provide a total-internal-reflection concentrator between the two lenses. The first and second emission light guides may be relatively close to each other or even touching. The first and second emission light guides may have central axes that extend at different angles.

According to a fifth aspect of the present disclosure, there is provided an excitation light guide unit for an assay device having a test portion and first and second light sources, the excitation light guide unit comprising:
 a first excitation light guide; and
 a second excitation light guide;
 wherein the first and second excitation light guides are formed in one-piece, and wherein the first excitation light guide is adapted to guide excitation light from the first light source to a first test zone of the test portion, and the second excitation light guide is adapted to guide excitation light from the second light source to a second test zone of the test portion.

According to a sixth aspect of the present disclosure, there is provided an excitation light guide unit for an assay device having a test portion and first and second light sources, the excitation light guide unit comprising:
 a first excitation light guide; and
 a second excitation light guide;
 wherein the first and second excitation light guides are fixed together, and wherein the first excitation light guide is adapted to guide excitation light from the first light source to a first test zone of the test portion, and the second excitation light guide is adapted to guide excitation light from the second light source to a second test zone of the test portion.

The excitation light guide unit and/or the first and second excitation light guides of the fifth and sixth aspects may be configured in accordance with the excitation light guide unit and/or the first and second excitation light guides described above with respect to the first and second aspects. For example, the excitation light guides may each comprise a light collimator lens adapted to locate adjacent the respective light source, in order to collimate light arriving from the light source into the excitation light guide. The excitation light guides may also comprise refractive and/or reflective surfaces. The excitation light guides may comprise a light exit face. At least one refractive and/or reflective surface may be provided at a substantially opposite side of each light guide to the light exit face. The at least one refractive and/or reflective surface may be curved. A best fit plane extending through the curved surface may be at an angle from the plane of the light exit face. The angle may be between about 20 and 70 degrees, or between 30 and 50 degrees or otherwise. The curved surface may extend substantially an entire length of the light guide. The refractive and/or reflective surfaces may act as a combined folding mirror and lens, providing optical power to the excitation light.

In one embodiment, the first and second excitation light guides are provided at substantially opposite ends of the excitation light guide unit and the excitation light guide unit comprises one or more elongate elements that connect the first and second excitation light guides together. In combination, the one or more elongate elements and the first and second light guide units may define a recess, e.g., a square or rectangular recess, therebetween. In one embodiment, the emission light guide is adapted to locate snugly within the recess.

BRIEF DESCRIPTION OF DRAWINGS

By way of example only, embodiments are now described with reference to the accompanying drawings, in which:

FIG. 4 shows an oblique view of a housing base employed in the device of FIG. 1;

FIG. 5a shows an oblique view of a test strip used in the assay device of FIG. 1; and FIG. 5b provides a schematic representation of the test strip including several regions that are arranged sequentially along the length of the strip of FIG. 5b;

DESCRIPTION OF EMBODIMENTS

Figure 1:
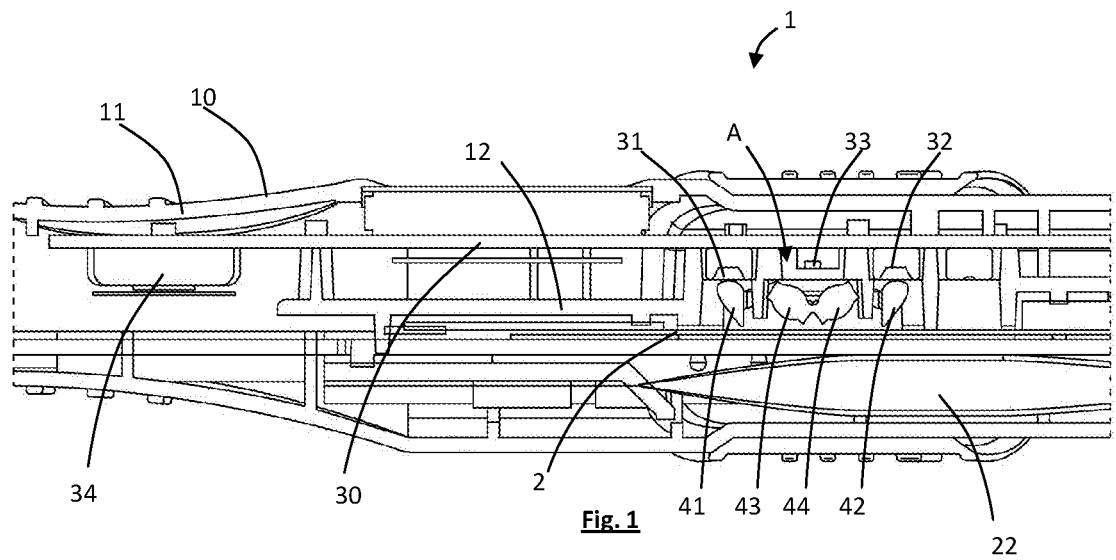
FIG. 1 shows a cross-sectional view of a portion of an assay device according to an embodiment of the present disclosure.

FIG. 1 shows a cross-sectional view of a portion of an assay device 1 according to a first embodiment of the present disclosure. The device 1 comprises a housing 10 including an outer casing 11 and an elongate base 12 located within the outer casing 11. The housing 10 defines an interior region in which a test portion, electronic circuitry and an optical assembly are located.

The base 12 of the housing is shown in more detail in FIG. 4. The base 12 includes a rear wall 13 and side walls 14 projecting from the edges of an inner surface 131 of the rear wall 13, which inner surface 131 of the rear wall and inner surfaces 141 of the side walls 14 define a recessed portion of the base 12. The recessed portion is substantially enclosed on one side by the test portion, more particularly, in this embodiment, a lateral flow test strip 2, as represented in FIG. 5a. Adjacent a first end 121 of the housing, a protuberance 132 projects from the inner surface 131 of the rear wall 13 and is adapted to fit into a registration hole 21 of the test strip 2. In combination with guide ribs and reliefs 15 formed in the housing base 12, the engagement between the protuberance 132 and the hole 21 in the test strip 2 serves to register the position of the test strip 2 relative to the base 12 and other components of the test device. The base 12 is connected to the outer casing 1 via screws which extend through screw holes 122 at opposite ends of the base 12.

As indicated, the test portion in this embodiment is provided by a lateral flow test strip 2. The lateral flow test strip 2 includes several regions that are arranged sequentially along the length of the strip, as represented schematically in FIG. 5b. The regions include a sample receiving region 2a, a label-holding region 2b, a test region 2c, and a sink 2d. The regions comprise chemically treated material such as chemically treated nitrocellulose, located on a waterproof layer. The design of the test strip 2 is such that a biological sample, when received and transferred from the sample receiving region 2a can transfer under capillary action into the label-holding region 2b, which contains a fluorescent substance for labelling target analytes in the sample, and into the test region 2c where the sample will contact first and second test zones (first and second test stripes 2e, 2f in this embodiment) which each contain an immobilized compound capable of specifically binding the target analytes or a complex that the target analytes and the fluorescent labelling substance form. The sink (absorbent) region 2d is provided to capture any excess sample. Transfer of the sample along the test strip 2 can be assisted using a buffer solution, e.g., a buffer solution released from a reservoir 22. The presence of the fluorescent labelled analyte in the sample generally results in at least one of the test stripes 2e, 2f at the test region 2c being excitable by light in a particular wavelength band such as to cause a detectable level of florescent emission light to be emitted by the fluorescent label in a different wavelength band. Depending on the degree of light detected it may be determined that the target analyte is present in the sample, and therefore a person providing the sample has a particular medical condition.

In this embodiment, the assay device 1 can be arranged to receive a biological sample, and combine the sample with buffer solution, substantially in accordance with the test device discussed in in PCT publication no. WO 2011/091473 A1, the content of which is incorporated herein by reference. For example, in accordance with FIGS. 8 to 14 of WO 2011/091473 A1, the assay device 1 can include two wings that extend from the housing and which are arranged to receive a biological sample, e.g., through a nose blow, the sample being transferred from the wings to the test strip under capillary action. The reservoir containing buffer solution may be released, in order to combine the buffer solution with the sample, by moving a slider along the housing. Nevertheless, the assay device of the present disclosure may take a variety of other configurations.

In this embodiment, the assay device 1 is configured to test for the presence of both influenza A and influenza B analytes in a biological sample. The first test stripe 2e is configured to bind fluorescent-labelled influenza A analyte, if the influenza A analyte is present in the sample, and the second test stripe 2f is configured to bind fluorescent-labelled influenza B analyte, if the influenza B analyte is present in the sample. Although not shown, a further control stripe may also be provided to indicate that a testing procedure has been performed. The control stripe can be located downstream of the first and second test stripes 2e, 2f to bind and retain the labelling substance. Detection of fluorescence at the control stripe can indicate that sample has flowed through the test region 2c.

In alternative embodiments, e.g., where a single target analyte is to be detected only, e.g., influenza A only, influenza B only, or an entirely different target analyte, the second test stripe 2f may be provided for use as a control stripe only. Nonetheless, where target analytes such as influenza A and influenza B are to be detected, in accordance with the present embodiment, since the presence of one of these analytes in a body is generally understood to be mutually exclusive of the presence of the other of these analytes in the body, one of the two test stripes 2e, 2f can be used to perform a control function. For example, background fluorescence or autofluorescence can be deduced from the test stripe that does not have a fluorescently labelled target analyte bound thereto, and the value of this fluorescence can be considered when determining a degree of fluorescence attributable to the presence of fluorescently labelled target analyte at the other of the test stripes 2e, 2f.

Figure 2:
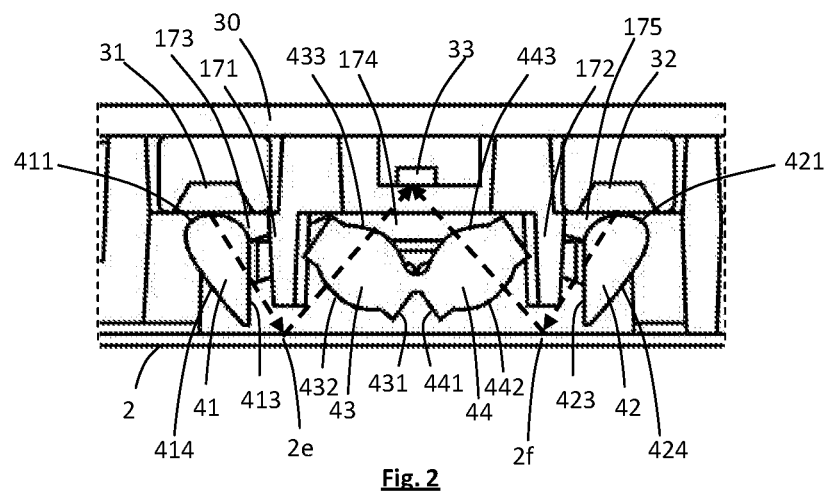
FIG. 2 shows a close-up of the cross-sectional view of FIG. 1 generally at a region indicated by reference A in FIG. 1.

Referring to FIGS. 1 and 2, the electronic circuitry includes a first light source, in particular a first LED 31, a second light source, in particular a second LED 32, and a light detector, in particular a photodetector 33. The photodetector 33 is positioned between the first and second LEDs 31, 32. The first LED 31 is adapted to illuminate the first test stripe 2e and the second LED 32 is adapted to illuminate the second test stripe 2f. The electronic circuitry includes a printed circuit board 30 connected to a battery and processing chip 34. The first and second LEDS 31, 32 and the photodetector 33 are located on and protrude from the circuit board 30. The circuit board 30 is positioned adjacent an opposite side of the rear wall 13 of the base 12 of the housing 1 from the test strip 2, between the base 12 and a portion of the casing 11. With reference to FIG. 4, access holes are provided in the rear wall 13 of the housing to allow light to transfer from the LEDS 31, 32 to the optical assembly 41-44, and from the optical assembly 41-44 to the photodetector 33. The Access holes include first and second LED access windows 133, 134 and a photodetector access window 135 positioned between the first and second LED access windows 133, 134.

The wavelength of light of the first and second LEDs 31, 32 is chosen so as to excite any fluorescent-labelled analytes that are bound at either of the first and second test stripes 2e, 2f, and therefore cause emission of fluorescent light from the test stripes 2e, 2f. The photodetector 33 is configured to detect the fluorescent emission light and, based on the strength of light detected, the processor of the device is adapted to make a determination about the presence of influenza A or influenza B in the biological sample.

In this embodiment, the photodetector 33 is effectively shared between the two LEDs 31, 32 and the two test stripes 2e, 2f. In order to differentiate between emission light from the first test stripe 2e and emission light from the second test stripe 2f, the LEDs 31, 32 may be adapted to illuminate the respective test stripes 2e, 2f at different times, e.g., sequentially. However, separate photodetectors 33 may be used in alternative embodiments.

Referring to FIGS. 1, 2 and 4, the optical assembly 41-44 is generally disposed between the electronic circuitry including the printed circuit board 30 and the lateral flow test strip 2, in a central recess of the base 12 defined between the inner surface 131 of the rear wall 13 of the base 12, the inner surfaces 141 of the side walls 14 of the base 12 and the inner surfaces 161 of two opposing inner walls 16 of the base 12, which are spaced apart in the elongate direction of the base 12.

Figure 3:
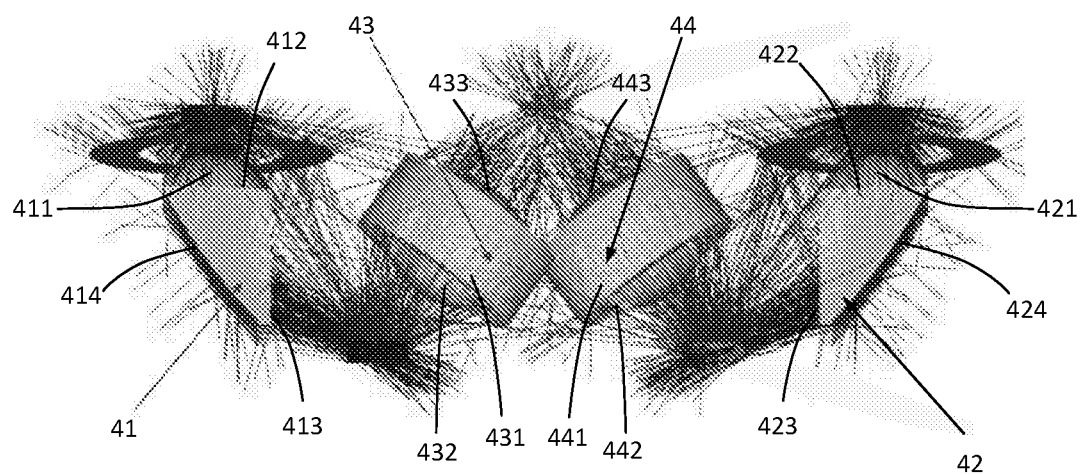
FIG. 3 shows a ray trace diagram for optical components of the device of FIG. 1.

Referring to FIG. 2, the optical assembly comprises first and second excitation light guides 41, 42 and first and second emission light guides 43, 44. The first excitation light guide 41 is adapted to guide excitation light from the first LED 31 to the first test stripe 2e and the second excitation light guide 42 is adapted to guide excitation light from the second LED 32 to the second test stripe 2f. The first emission light guide 43 is adapted to guide fluorescent emission light from the first test stripe 2e to the photodetector 33 and the second emission light guide 44 is adapted to guide fluorescent emission light from the second test stripe 2f to the photodetector 33. Path directions of the light are represented very generally using dotted arrows in FIG. 2. FIG. 2 shows a close up view of the device 1 at a region indicated by reference A in FIG. 1. A ray-trace diagram, shown in FIG. 3, provides a more detailed representation of excitation and emission light travelling through the optical assembly.

The excitation and emission light guides 41, 42, 43, 44 perform multiple functions. For example, in addition to guiding light to and from the test stripes 2e, 2f, the light guides perform spectral filtering and focus, collimate and/or diverge light.

Each excitation light guide 41, 42 includes a convex light collimator lens 411, 421 positioned on a first end face 412, 422 of the light guide adjacent the respective light source 31, 32. The collimator lenses 411, 421 are configured to collimate light arriving from the respective light source 31, 32 into the excitation light guide 41, 42. Each excitation light guide 41, 42 also includes a light exit face 413, 423 and a light focusing reflector face 414, 424, which each extend towards the test strip 2 from opposite edges of the first end face 412, 422. The light exit face 413, 423 extends substantially perpendicular to the test strip 2, whereas the reflector face 414, 424 extends at an acute angle relative to the test strip 2. As the light exit face 413, 423 and the reflector face 414, 424 extend from the first end face 414, 424, they converge together, giving the excitation light guides 41, 42 a substantially wedge shaped configuration. A best fit plane extending through the reflector surface 414, 424 is at an angle from the plane of the light exit face of about 30 to 50 degrees, e.g., about 40 degrees. In general, the first and second excitation light guides 41, 42 are configured to route excitation light efficiently from the first and second LEDs 31, 32 to the first and second test stripes 2e, 2f, respectively. The reflector surface 414, 424 provides a combined mirror and lens in this embodiment, giving optical power to the excitation light as it passes through the excitation light guides 41, 42.

Each emission light guide 43, 44 includes a cylindrical body 431, 441 (or 'spacer') with first and second end surfaces. The first and second end surfaces are provided with first and second convex lenses 432, 433, 442, 443, respectively, which lenses are adapted to focus light into and out of the body 431, 441. The convex lenses may be ball lenses, half ball lenses or plano-convex lenses). While most light may be transferred directly between the two convex lenses 432, 433, 442, 443 of each emission light guide 43, 44, some light may also be routed by total internal reflection (TIR) within the cylindrical body 431, 441.

Figure 6A:
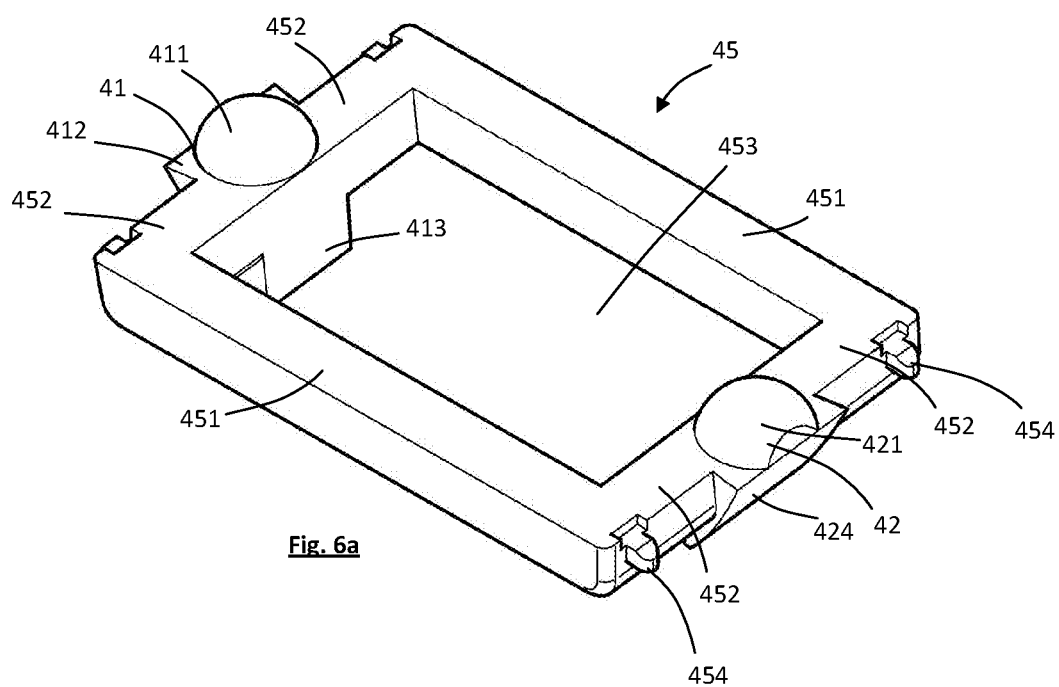
FIGS. 6a and 6b show top and bottom oblique views, respectively, of an excitation light guide unit employed in the device of FIG. 1.
Figure 6B:
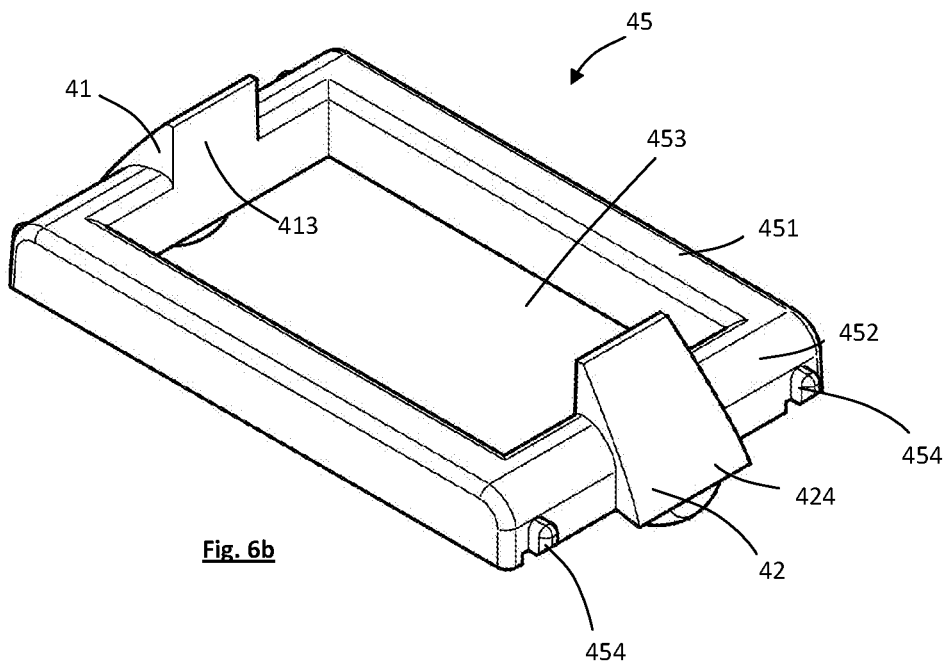
Figure 7A:
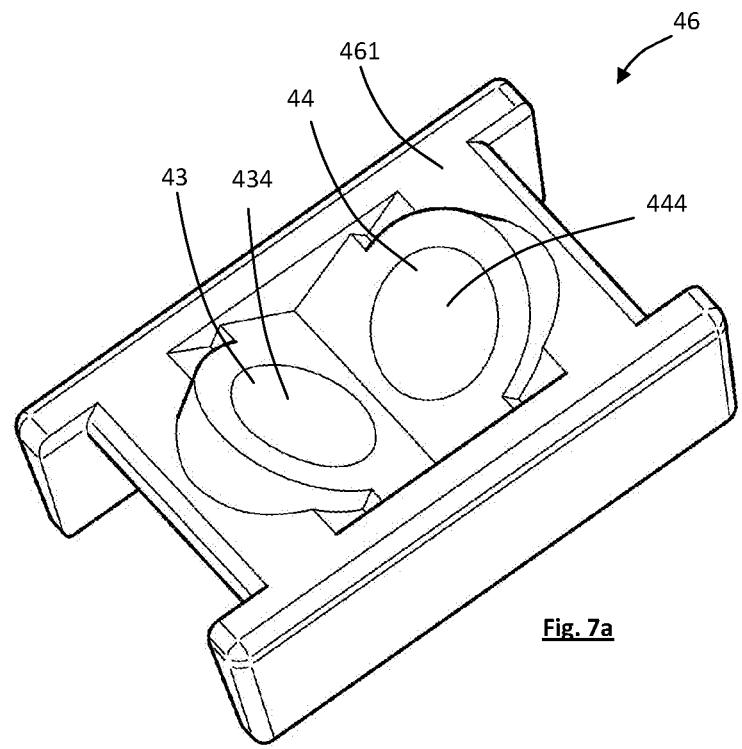
FIGS. 7a and 7b show top and bottom oblique views, respectively, of an emission light guide unit employed in the device of FIG. 1.
Figure 7B:
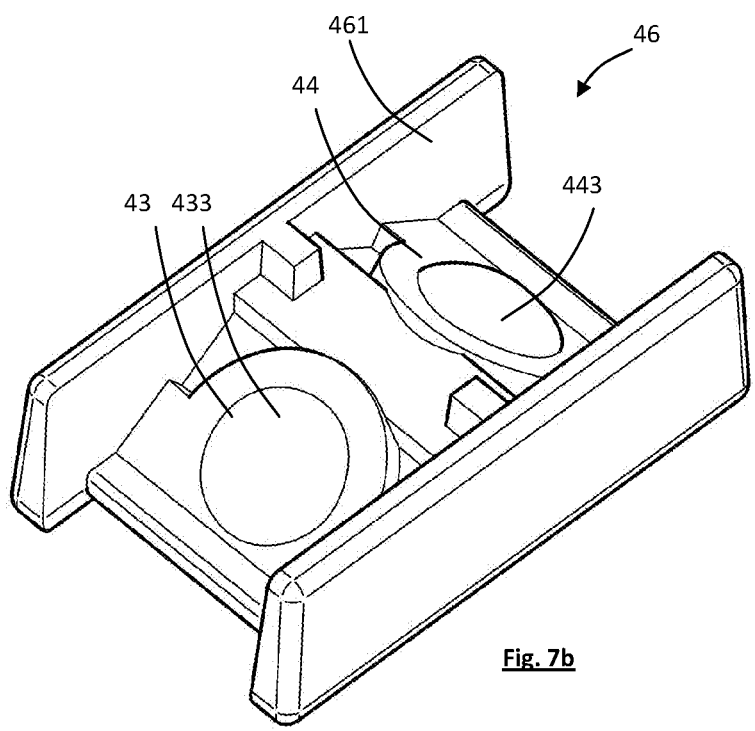

With reference to FIGS. 6a and 6b, the first and second excitation light guides 41, 42 are formed in one-piece, integrated into an excitation light guide unit 45. Similarly, with reference to FIGS. 7a and 7b the first and second emission light guides 43, 44 are formed in one-piece, integrated into an emission light guide unit 46. Both the excitation light guide unit and the emission light guide unit are formed of a respective homogenous material.

By forming the excitation light guides 41, 42 in one-piece, and the emission light guides 43, 44 in one piece, these components of the optical assembly provide larger single components than if formed separately, and are therefore easier to handle and assemble during the manufacturing process.

The emission light guide unit 46 is adapted to be fitted into the excitation light guide unit 45. The excitation light guides 41, 42 are provided at substantially opposite ends of the excitation light guide unit 45 and the excitation light guide unit 45 comprises two elongate elements, in particular ties bars 451, that extend from shoulder portions 452 either side of each of the excitation light guides 41, 42 to connect the first and second excitation light guides 41, 42 together. In combination, the two tie bars 451, the shoulder portions 452, and the excitation light guides 41, 42 define a recess 453 therebetween. The emission light guide unit 46 is adapted to be fitted snugly in the recess 453. Tabs 454 project from corners of the excitation light guide unit 45 to securely engage the excitation light guide unit 45 with the base 12 of the housing 10.

The emission light guide unit 46 comprises a structure 461 that substantially surrounds the emission light guides 43, 44, and provides datum surfaces to fit within the recess 453 of the excitation light guide unit 45 and position against other components of the device 1.

Referring to FIGS. 2 and 4, the base 12 of the housing includes first and second light baffles 171, 172, which project from the inner surface 131 of the rear wall 13 of the base 12. The baffles 171, 172 are provided between the LEDs 31, 32 and the photodetector 33, to prevent or reduce direct light transfer between the LEDs 31, 32 and the photodetector 33. Distal ends of the first and second light baffles 171, 172 terminate short of the lateral flow test strip 2, substantially in line with the first and second test stripes 2e, 2f, to create openings between chambers that are defined between the light baffles 171, 172.

In more detail, the light baffles 171, 172 divide the central recess of the base 12 of the housing 1 into first, second and third chambers 173, 174, 175. The first chamber 173 and the second chamber 174 are separated by the first light baffle 171, and the second chamber 174 and the third chamber 175 are separated by the second light baffle 172. The first LED access window 133 opens into the first chamber 173, the photodetector access window 135 opens into the second chamber 174, and the second LED access 134 opens into the third chamber 175. The first test stripe 2e is positioned at the opening between the first chamber 173 and the second chamber 174, and the second test stripe 2f is positioned at the opening between the second chamber 174 and the third chamber 175. The first excitation light guide 41 is positioned in the first chamber 173, the second excitation light guide is positioned in the third chamber 175, and the first and second emission light guides 43, 44 are both positioned in the second chamber 174, between the first and third chambers 173, 175.

In this embodiment, the device 1 provides a rapid flu test (RFT), including a relatively low cost, inherently disposable, and high performance optical reader for a test strip 2. The device can digitise a pair of fluorescently labelled test stripes 2e, 2f and also a control stripe (via a subsidiary sensor arrangement not shown). The device employs an immunochromatographic (lateral flow) test strip 2 but can be adapted to alternative formats.

A function of the light guides 41, 42, 43, 44 is to provide efficient routing of light from the LEDs 31, 32 to the test strip 2 and from the test strip 2 to the photodetector 33. A further function is to provide spectral selection. The light guides 41, 42, 43, 44 take a very compact, thin form, compatible with volume and low cost manufacture.

In order to route the light efficiently, the light guides 41, 42, 43, 44 in this embodiment use a combination of refractive surfaces and reflective surfaces. By employing refractive surfaces, e.g., in the emission light guides 43, 44, for example, total internal reflection (TIR) can be used, obviating the need for, and associated cost of, metallised (or equivalent) high reflectivity coatings.

In the assay device of the present embodiment, the choice of fluorescent label is made in view of a range of considerations, including: the excitation wavelength band of the label (which affects the choice of light source and its associated power and cost); the absorptivity of the label, the efficiency of the label, e.g., quantum efficiency, of the label; the emission wavelength band of the label, (which affects the choice and cost of filters to separate the emission light from the excitation light), and the assay integration compatibility.

The fluorescent reader assembly described herein relies on being able to separate relatively strong excitation light from relatively weak fluorescent emission light, by virtue of their different wavelengths. Selective spectral filters (provided by the light guides) are used at least in part to achieve this.

While traditional fluorescent labels may be used in embodiments of the present disclosure, they can exhibit relatively small Stokes shifts (i.e. a relatively small wavelength shift between the emission and excitation wavelength bands) and this places strong demands on filters, which can in turn translate to more expensive parts. It can also place stringent demands on all materials in the system to avoid contamination of the emission wavelength band by auto-fluorescence which typically exhibits small Stokes shifts.

It has therefore been found highly advantageous in embodiments of the present disclosure to operate the device with fluorescence based on larger (effective) Stokes shifts. Fluorophores that have been found to exhibit particularly large Stokes shifts are quantum dots, which are semiconductor nanoparticles, specifically engineered to create a particular excitation and emission response. Collectively, quantum dots can also offer relatively high absorption in the 'short blue' spectrum (which is conveniently accessible to low cost LEDs) and provides high quantum efficiency. Therefore, quantum dots have been determined as an appropriate fluorescent label according to the present disclosure, albeit other types of fluorescent labels could be used.

Figure 8:
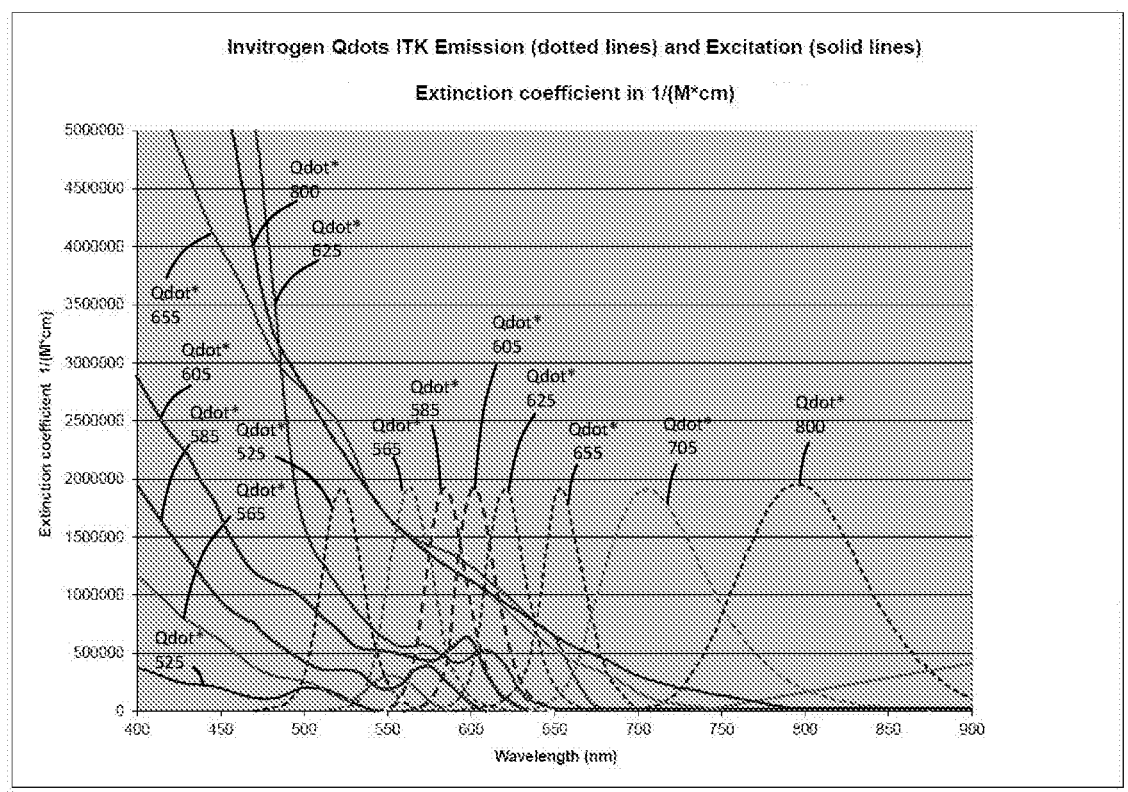
FIG. 8 shows plots of excitation and emission spectra of quantum dots that may be used in embodiments of the present disclosure.

The label that is used in the assay device according to the present embodiment is a quantum dot with an emission wavelength band peak of 800 nm, in particular the Invitrogen™ Qdot™ 800. Referring to FIG. 8, which shows quantum dot excitation and emission spectra, the Qdot™ 800 exhibits the longest Stokes shift of the quantum dots tested. This relatively high degree of shift simplifies filter choice and reduces auto-fluorescent contamination. Nonetheless, quantum dots with different excitation and emission spectra, e.g., as per any one of the quantum dots identified in FIG. 8, may be employed in embodiments of the present disclosure.

In the assay device of the present embodiment, the choice of light source, e.g., LED, has been made in view of a range of considerations, including: the absorptivity of the selected fluorescent label at the light source's operating wavelength; total radiant power at the maximum available drive current for the device; the available area of the electronic circuitry, and the device cost. When using the Qdot™ 800, absorptivity of about 350 nm is favoured, for example. However, an excitation wavelength band centred above or below 350 nm may be used, e.g., between 325 to 500 nm, between 350 nm to 450 nm, or otherwise. LEDs of higher wavelength can have lower manufacturing costs, and, while the higher wavelengths may not be most optimally absorbed by the fluorescent label, the may still be sufficiently absorbed by the fluorescent label for the purposes of the present disclosure.

LEDs selected for use in the assay device according to the present embodiment are surface mounted LEDs that emit at 420 nm. They provide high radiant power at a 10 mA operating current and compatibility with other components of the device. Nevertheless, as indicated, LEDs or other light sources having a variety of different wavelengths can be used.

As discussed, high discrimination between the emission and excitation wavelength bands by the light guides is desirable. There can therefore be high acceptance of light in the emission wavelength band at the photodetector and high rejection of light in the excitation wavelength band at the photodetector (in addition to high rejection of any excitation component that could overlap with emission band at the light source). In the present embodiment, this is achieved using light guides that provide spectral filtering. In particular, the first and second excitation light guides offer high transmission of light in the excitation wavelength band whilst blocking longer wavelength light (i.e. they act as short pass filters) and the first and second emission light guides offer high transmission of light in the emission wavelength band whilst blocking shorter wavelength light (i.e. they act as long pass filters).

Spectral filtering in the light guides of the present embodiment is achieved by integrating spectral filtering dyes into resins that form the excitation and emission light guides. The light guides in this embodiment are formed of thermoplastic injection moulded polycarbonate, and the dyes are incorporated during the moulding procedure. Integration of the filters into the light guides, rather than providing separate filter elements and/or filter coatings, can provide significant simplification of the assay device assembly process. Nonetheless, it is conceived that separate filter elements and/or coatings may be used in alternative embodiment of the present disclosure.

Figure 9A:
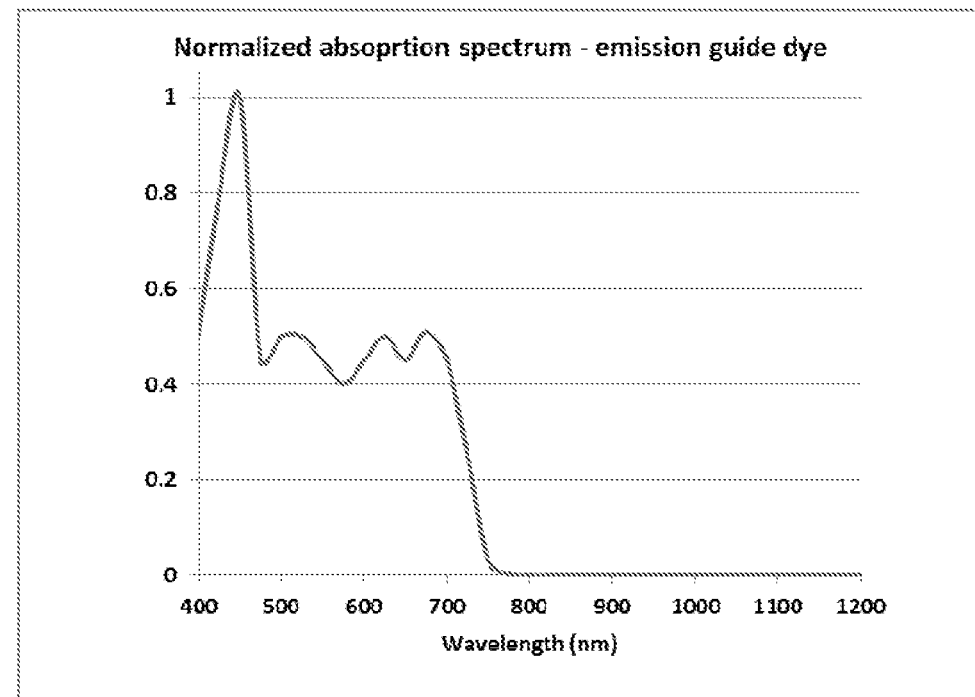
FIGS. 9a and 9b show plots of spectral absorption characteristics of dyes used in the emission and excitation light guides, respectively, of the device of FIG. 1.
Figure 9B:
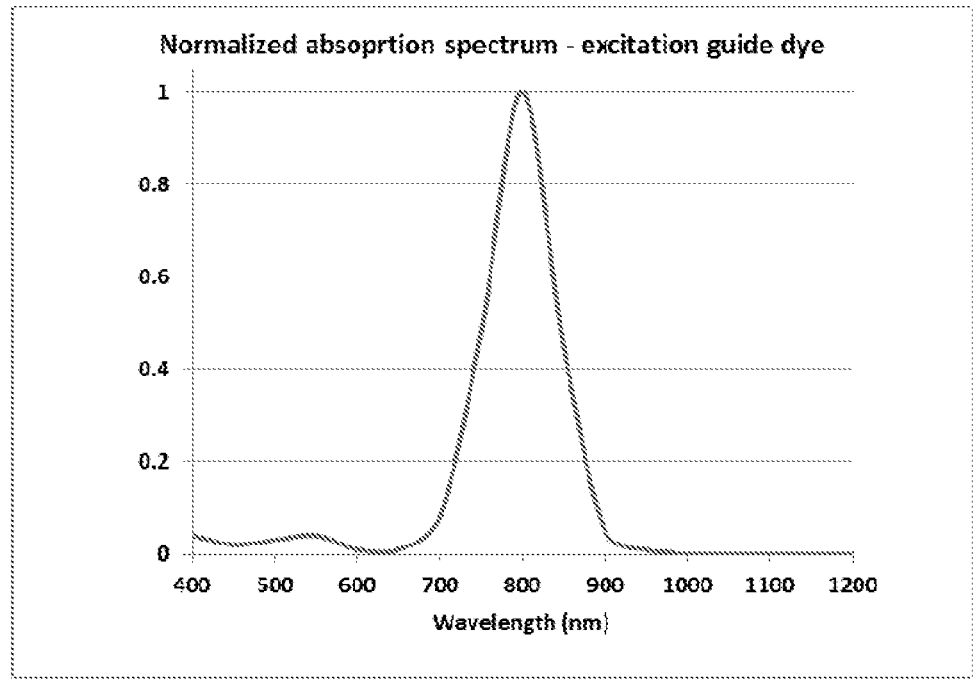

Spectral absorption characteristics of dyes used in the embodiment of the present disclosure are represented graphically in FIGS. 9a and 9b. FIG. 9a shows absorption spectra of the first dye material used in the emission light guides, and FIG. 9b shows absorption spectra of the second dye material used in the excitation light guides. The first dye material blocks light with wavelength from 350 to 700 nm and allows transmittance of light with wavelength above 750 nm. The second dye material blocks light with wavelength of a relatively narrow band around 800 nm and allows transmittance of light with wavelength outside of this band.

The incorporation of dyes into the thermoplastic creates spectral filters by imparting spectrally varying absorption. The underlying mechanism is that as governed by the Beer Lambert law which relates absorbance to the spectral absorptivity (i.e. the particular response of a particular dye), the concentration of the dye and the propagation distance through the dyed part.

Because absorbance depends on the path length or propagation distance, it is desirable that possible path lengths through the light guides conform to a reasonably narrow distribution; otherwise, the guides will either exhibit leakage paths (overly short paths with lower than intended absorption) or undue loss (overly long paths with higher than intended absorption).

Figure 10A:
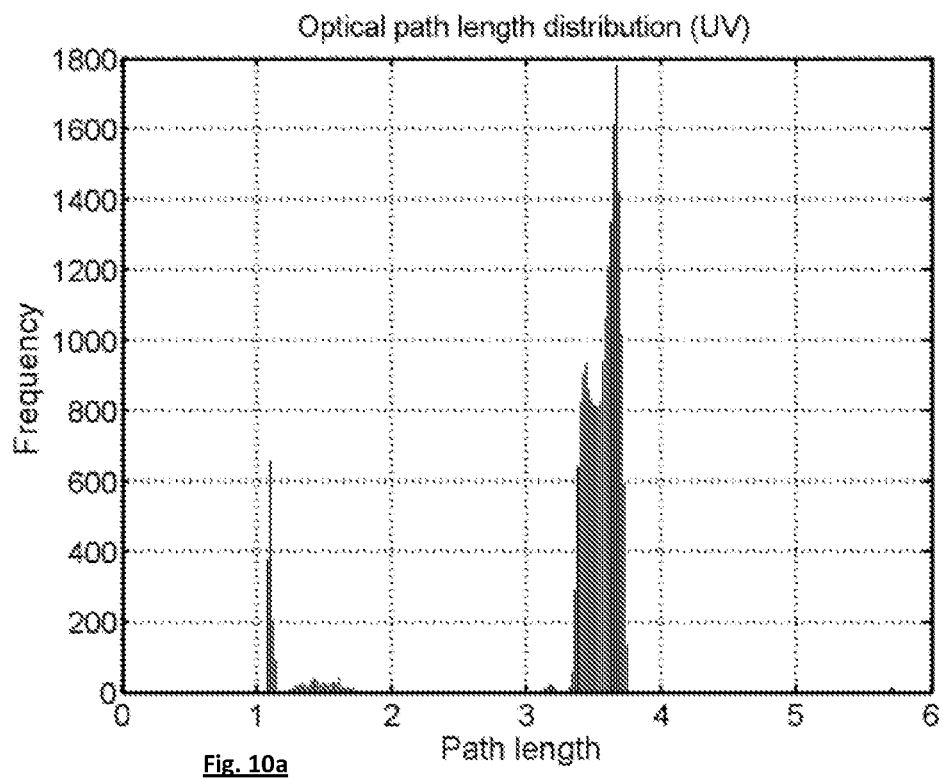
FIGS. 10a and 10b show plots of path length distributions of the light guides of the device of FIG. 1.
Figure 10B:
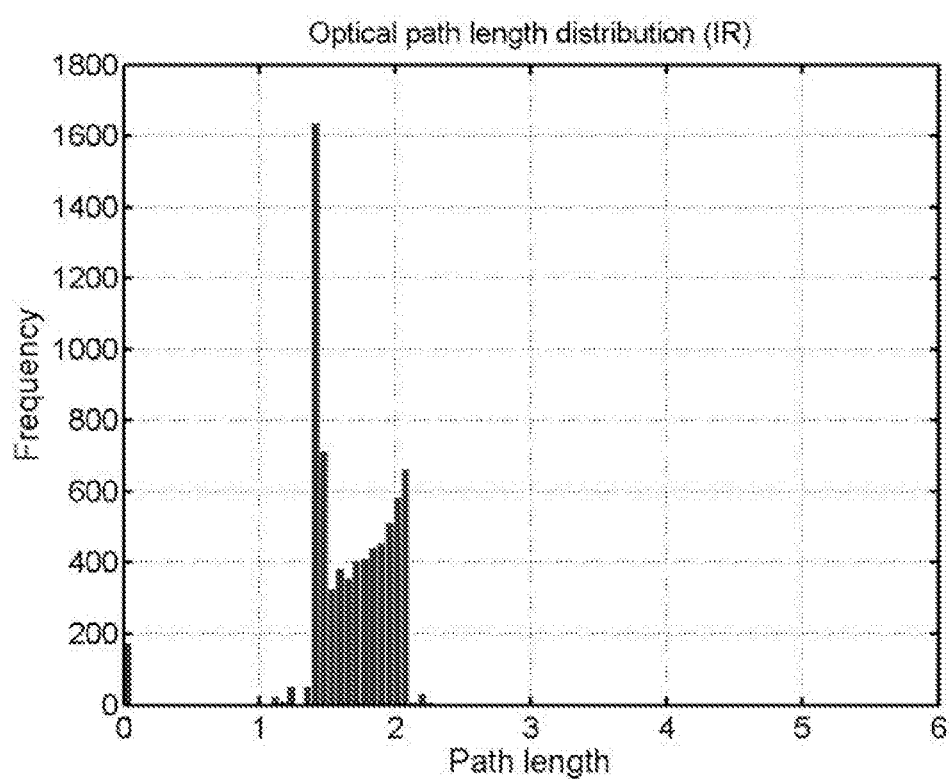

The optical paths in the light guides of the assay device of the present embodiment have been analysed to confirm that they exhibit suitably narrow path length distributions as evidenced graphically by the plots in FIGS. 10a and 10b (showing path lengths for the excitation light guide and the emission light guide, respectively).

Narrow path length distributions are generally a characteristic of image forming systems and, whilst the light guides are not required to form images, each uses optical surfaces to route the light in a geometry that approximates to that of an imaging forming system. As a result the distributions are narrow and the filter characteristics are relatively independent of ray trajectory through the part.

In the present embodiment, the test strip is the primary 'transducer' that converts the target analytes (influenza A and B, or more particularly, nucleoproteins for influenza A and B) to, in essence, a density of Qdot 800 labels at pre-defined capture stripes 2e, 2f. In a fixed optics reader, it is essential that tight registration is achieved such that the fixed reader is centred on the stripes. In the present embodiment, this is achieved by using the housing 1, including the base 12, as a mechanical hub. Registration of the optics to the signal stripes is achieved at least in part by the protruberance 132 and the registration hole 21 of the test strip 2 (a form of pin and hole interface). The same hole can be used during test strip manufacture to register the positions of the test stripes 2e, 2f, relative to the stripes dispensing equipment.

Fluorescence detection requires the ability to measure very low light levels. In the present embodiment, the photodetector is a light to frequency converter. Ultimately, the photodetector can generate an electrical signal indicative of the strength of the fluorescent emission light that it detects from each of the first and second test stripes 2e, 2f, which signal is received by a processor 34 in the device 1. The amount of the target analyte can be determined by the processor correlating the strength of the fluorescent emission light to a predetermined target analyte concentration. However, the strength of the fluorescent emission light of one test stripe can also be compared by the processor with the strength of the fluorescent emission light of the other test stripe.

For example, one process that can be employed by the present embodiment, relies on the fact that influenza A and B are mutually exclusive, or are at least very rarely seen in combination. Thus it can be expected that the result of the assay device will either be: influenza A positive or influenza B positive or neither influenza A or B positive. On this basis, the process can comprise:

measuring optical intensity signals at the first and second test stripes (the A & B lines), when the test strip is still dry, e.g., when the sample/buffer solution has not developed along the strip;

monitoring optical intensity signals at the A & B lines during development (e.g., to check for correct operation and to judge when the test is complete);

measuring optical intensity signals at the A & B lines at completion of the development;

normalising the A & B optical intensity signals using the dry values where this assumes that any background is common to the two channels;

calculating the difference in the two signal intensities and comparing the magnitude of the difference against a pre-set threshold whilst using the sign to distinguish between A or B being positive The approach may provide for robust measurement and permit use of a lower threshold for greater sensitivity.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An assay device comprising:
    a housing; and
    a test portion, electronic circuitry and an optical assembly, each at least partially located in the housing;
    wherein:
    the test portion comprises at least first and second test zones, the first and second test zones being spaced apart in a first direction of the device and adapted to receive an analyte and one or more fluorescent labels associated with the analyte, the fluorescent labels being excitable by excitation light and adapted to emit emission light upon excitation by excitation light;

the electronic circuitry comprises at least first and second light sources and one or more light detectors, the one or more light detectors being located between the first and second light sources in the first direction of the device;

the optical assembly comprises at least first and second excitation light guides and at least first and second emission light guides, wherein the first excitation light guide is adapted to guide excitation light from the first light source to the first test zone, and the first emission light guide is adapted to guide emission light from the first test zone to the one or more light detectors, and the second excitation light guide is adapted to guide excitation light from the second light source to the second test zone, and the second emission light guide is adapted to guide emission light from the second test zone to the one or more light detectors; and the first and second excitation light guides are connected together by first and second elongate elements which extend in the first direction between the first and second excitation light guides, wherein:

the first elongate element extends from a shoulder portion at a first side of the first excitation light guide to a shoulder portion at a first side of the second excitation light guide; and the second elongate element extends from a shoulder portion at a second side of the first excitation light guide to a shoulder portion at a second side of the second excitation light guide; and the first and second elongate elements, shoulder portions, and first and second excitation light guides define therebetween a recess in which the first and second emission light guides are received.

2. The device of claim 1, wherein the excitation and emission light guides perform one or more of focusing, collimating and diverging light.

3. The device of claim 1, wherein at least one of the excitation or emission light guides provides spectral filtering.

4. The device of claim 3, wherein the excitation light guides provide a short pass filter and the emission light guides provide a long pass filter.

5. The device of claim 1, wherein at least one of the excitation or emission light guides comprise a light transmitting material impregnated with a spectral filtering dye.

6. The device of claim 1, wherein the fluorescent labels of the test portion are configured such that an excitation wavelength band of the excitation light and an emission wavelength band of the emission light have peak wavelengths that are at least 200 nm apart, or at least 250 nm apart, or at least 300 nm apart, or at least 350 nm apart.

7. The device of claim 1, wherein an excitation wavelength band of the excitation light has a peak wavelength between 325 and 500 nm.

8. The device of claim 1, wherein the fluorescent labels of the test portion are configured such that an emission wavelength band of the emission light has a peak wavelength between 650 and 850 nm.

9. The device of claim 1, wherein the fluorescent labels of the test portion are configured such that an excitation wavelength band of the excitation light has a peak wavelength of about 420 nm and an emission wavelength band of the emission light has a peak wavelength of about 800 nm.

10. The device of claim 1, wherein each of the fluorescent labels is a quantum dot.

11. An assay device comprising:
a housing; and
a test portion, electronic circuitry and an optical assembly, each at least partially located in the housing; wherein the test portion comprises:
a plurality of fluorescent quantum dots adapted to associate with at least one analyte, the quantum dots being configured to emit fluorescent emission light at a peak wavelength of 650 nm or greater, and
one or more test zones;
wherein the one or more test zones are adapted to receive the analyte and the fluorescent quantum dots associated with the analyte;
wherein the electronic circuitry comprises one or more light sources to provide excitation light to the one or more test zones, and one or more light detectors to detect fluorescent emission light from the quantum dots at the one or more test zones; and
wherein the optical assembly comprises:
an excitation light guide unit that comprises one or more excitation light guides adapted to guide the excitation light from the one or more light sources to the one or more test zones, and an emission light guide unit that comprises one or more emission light guides adapted to guide emission light from the one or more test zones to the one or more light detectors, wherein:
the excitation light guide unit comprises first and second excitation light guides connected together by first and second elongate elements wherein:
the first elongate element extends from a shoulder portion at a first side of the first excitation light guide to a shoulder portion at a first side of the second excitation light guide: and
the second elongate element extends from a shoulder portion at a second side of the first excitation light guide to a shoulder portion at a second side of the second excitation light guide; and
the first and second elongate elements, shoulder portions, and first and second excitation light guides define therebetween a recess in which the emission light guide unit is located.

12. The device of claim 11, wherein the quantum dot has a peak emission wavelength that is greater than 700 nm or greater than 750 nm.

13. The device of claim 11, wherein the quantum dot has a peak emission wavelength of about 800 nm.

14. The device of claim 1 wherein the housing comprises a first light baffle between the first light source and the one or more light detectors, and a second light baffle between the second light source and the one or more light detectors.

15. The device of claim 1, wherein the first excitation light guide comprises a first light collimator lens adjacent the first light source and the second excitation light guide comprises a second light collimator lens adjacent the second light source.

16. The device of claim 1, wherein the first and second excitation light guides each comprise refractive and/or reflective surfaces.

17. The device of claim 1, wherein one or more of the first and second excitation light guides is wedge-shaped.

18. The device of claim 1, wherein one or more of the first and second excitation light guides provides optical power.

19. The device of claim 1, a first lens is located at a first end of the first emission light guide, a second lens is located at a second end of the first emission light guide; a third lens is located at a first end of the second emission light guide and a fourth lens is located at a second end of the second emission light guide.

20. The device of claim 19, wherein the first emission light guide comprises a spacer between the first and second lenses and the second emission light guide comprises a spacer between the third and fourth lenses.

21. The device of claim 20, wherein the spacer of each of the first and second emission light guides is cylindrical.

22. The device of claim 1, wherein the first test zone is adapted to receive an influenza A analyte and the second test zone is adapted to receive an influenza B analyte.

23. The device of claim 1, wherein the one or more light detectors comprise a first light detector and wherein the first emission light guide is adapted to guide emission light from the first test zone to the first light detector and the second emission light guide is adapted to guide emission light from the second test zone to the first light detector.

24. The device of claim 1, wherein the device is a hand-held device.

25. The device of claim 1, wherein the test portion is fixed relative to the electronic circuit and the optical assembly prior to receipt of a biological sample.

26. The device of claim 1, comprising a one-piece excitation light guide unit, the first and second excitation light guides, shoulder portions and first and second elongate elements being integrally formed in the one-piece excitation light guide unit.

27. The device of claim 1, comprising a one-piece emission light guide unit, the first and second emission light guides being integrally formed in the one-piece emission light guide unit.

28. The device of claim 1, wherein the first and second excitation light guides are provided at substantially opposite ends of an excitation light guide unit and the excitation light guide unit comprises the first and second elongate elements that connect the first and second excitation light guides together and which at least partially define the recess therebetween.

29. The device of claim 1, wherein the test portion comprises a labelling portion comprising plurality of fluorescent labels, the test portion being configured to associate the one or more fluorescent labels with the analyte at the labelling portion.

30. The device of claim 1, wherein a supporting frame substantially surrounds the first and second emission light guides, the supporting frame providing datum surfaces to fit within the recess of the excitation light guide unit.

* * * * *